United States Patent [19]

Kötzsch et al.

[11] 4,370,204
[45] Jan. 25, 1983

[54] METHOD FOR THE PURIFICATION OF HEXAMETHYLDISILOXANE

[75] Inventors: Hans-Joachim Kötzsch, Reinfelden; Hans-Joachim Vahlensieck, Wehr, both of Fed. Rep. of Germany

[73] Assignee: Dynamit Nobel AG, Troisdorf, Fed. Rep. of Germany

[21] Appl. No.: 354,466

[22] Filed: Mar. 3, 1982

[30] Foreign Application Priority Data

Mar. 5, 1981 [DE] Fed. Rep. of Germany ....... 3108235

[51] Int. Cl.³ ............................................. B01D 3/36
[52] U.S. Cl. ...................................... 203/39; 203/57; 203/71; 556/456
[58] Field of Search ........................ 203/57, 59, 39, 71, 203/73, 80, 81, DIG. 3; 528/10, 20, 29; 556/456

[56] References Cited

U.S. PATENT DOCUMENTS 4,210,496 7/1980 Wong ................................. 556/456

OTHER PUBLICATIONS

"Azeotropic Data–III"; Advances in Chemistry Series 116; American Chemical Society; 1973; pp. 202–212.

*Primary Examiner*—Frank Sever
*Attorney, Agent, or Firm*—Felfe & Lynch

[57] ABSTRACT

Process for purifying hexamethyldisiloxane contaminated with toluene or other solvents that cannot be completely separated from the hexamethyldisiloxane by distillation, based on the discovery that hexamethyldisiloxane forms a previously unknown azeotrope with acetonitrile. This azeotrope has a heavier phase that is rich in acetonitrile and a lighter phase that is rich in hexamethyldisiloxane. These phases are mutually immiscible. The azeotrope starts to boil at 71.4° C., which permits the hexamethyldisiloxane to be separated at relatively low temperatures from the impurities. The process involves one or more entrainment distillations in the presence of an excess of acetonitrile and the re-separation of the acetonitrile from the resulting lighter phase by distillation. Two further novel azeotropic systems, one consisting of hexamethyldisiloxane and toluene and the other of acetonitrile and toluene, are provided.

5 Claims, 1 Drawing Figure

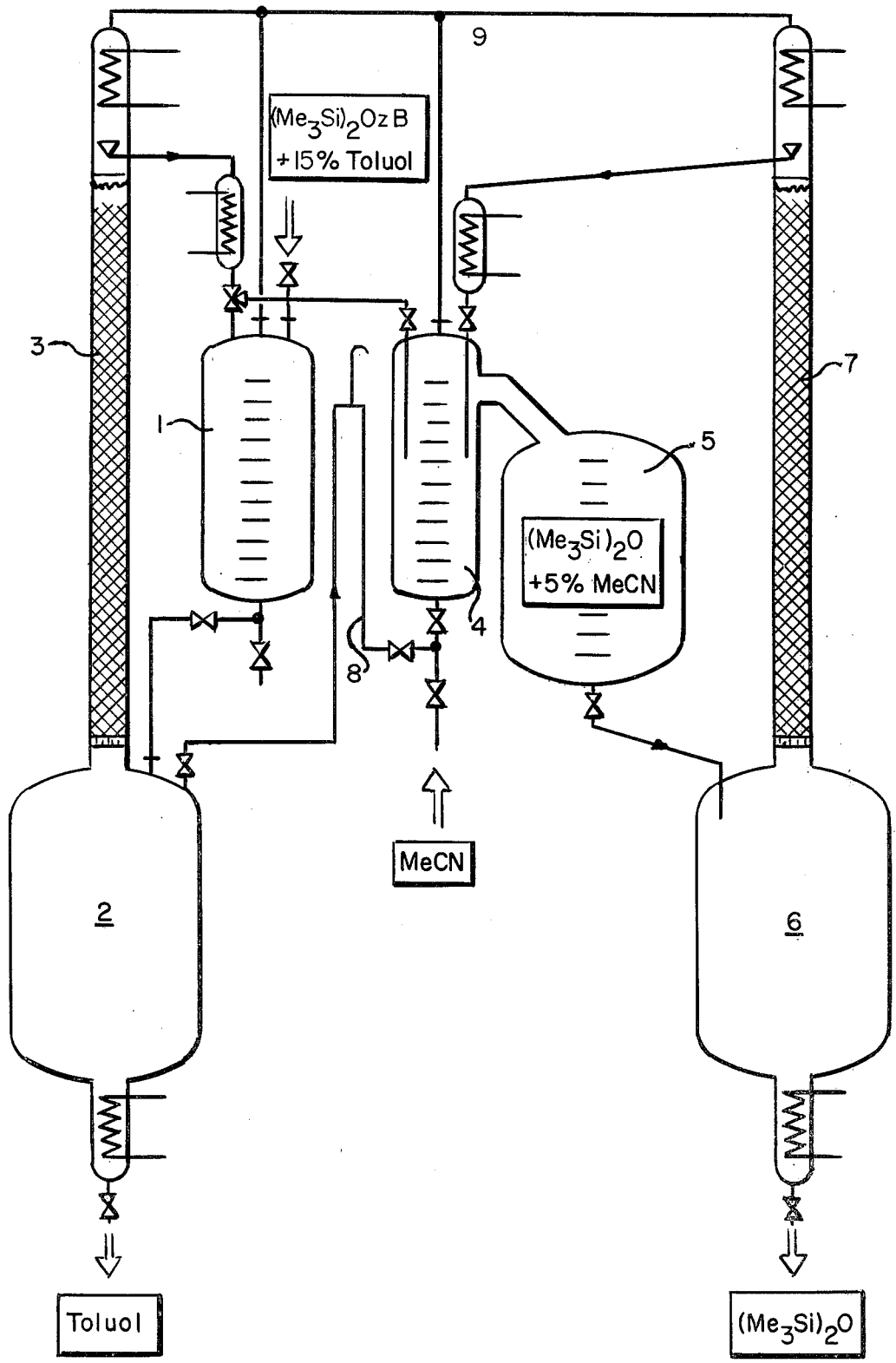

METHOD FOR THE PURIFICATION OF HEXAMETHYLDISILOXANE

This invention relates to a method for purifying hexamethyldisiloxane and azeotropic mixtures thereof. The process is particularly suited and preferably employed for purifying hexamethyldisiloxane contaminated with compounds that cannot be completely separated by distillation. In additional aspect the invention relates to the azeotropic mixtures that occur as by-products in the process.

The industrial manufacture of semisynthetic penicillins necessarily results in a considerable by-product of homogeneous mixtures of hexamethyldisiloxane and toluene. The siloxane derives from the separated protective groups that shield the penicillin precursors during synthesis, the toluene from its use as a solvent.

Since both of these materials are such valuable key chemicals, the ability to reemploy them is highly desirable. The toluene, for example, can not only be reintroduced as a solvent but can also be employed as a starting material for many important industrial sulfonating, nitrating, halogenating, oxidating, and coupling products in aromatic chemistry, while the hexamethyldisiloxane can be used for example in silicone chemistry to introduce trimethylsilyl terminal groups and on an industrial scale for the anhydrous saponification of aromatic halomethane groups involving the formation of the difficultly accessible and valuable trimethylchlorosilane.

For most purposes, in which only one component is exploited at a time, the mixture of siloxane and toluene can, however, not be utilized because the other components that are always present are disruptive. When chloromethyl aromatics are used to break down the siloxane into trimethylchlorosilane for example, the toluene gives rise to extremely undesirable Friedel-Crafts side reactions that lead to considerably lower yields and materials loss at the aromatic-product end.

Using distillation to separate the toluene and hexamethyldisiloxane has always made for problems in the past. On the one hand, their boiling points are only 10° C. apart and, on the other, a pure hexamethyldisiloxane has never been obtained, even in columns with many stages, but only one that stubbornly held on to its residual toluene. Furthermore, direct distillational separation incurs the risk of entraining other contaminants, like nitrogenous and sulfurous compounds, into the distillate when the former is distilled at 100° C.

There exists, then, a need for a process for obtaining pure hexamethyldisiloxane from a starting material consisting of hexamethyldisiloxane that contains impurities like toluene and/or other solvents along with any of the by-products that occur in the manufacture of semisynthetic penicillin.

The immediately obvious solution of isolating the hexamethyldisiloxane (and the toluene as well) in a column with a high plate number and high reflux ratio has not turned out to be successful. It has led to a previously unknown azeotrope of toluene and hexamethyldisiloxane with a boiling point of 99.1° C. and consisting of 1.4% toluene and 98.6% hexamethyldisiloxane. The existence of this azeotrope confirms both that the column-distillation route leads only to partial separation and enrichment at the expense of the azeotrope and that the ordinarily high initial concentration of toluene employed in practice will mean that the hexamethyldisiloxane can be obtained almost exclusively only in an azeotropic form.

In attempting to comply with the need described above, however, it has been discovered that it is simple to eliminate the problems encountered in separating hexamethyldisiloxane from mixtures of that substance with toluene and/or other solvents by distilling the hexamethyldisiloxane off in the form of an azeotrope with acetonitrile, separating the specifically lighter phase from the azeotrope, and harvesting the hexamethyldisiloxane by distillational separation of the acetonitrile.

The process in accordance with the invention relies on the fact that acetonitrile forms two further, long unknown azeotropes that were also discovered in the attempts described above:

1. The hexamethyldisiloxane-and-acetonitrile azeotrope (I) consists of approximately 63.5% by weight of hexamethyldisiloxane and approximately 35.5% by weight of acetonitrile. It boils under normal pressure at 71.4° C. and separates, surprisingly, into two liquid, mutually immiscible phases. The upper and lighter phase (II) consists of approximately 95% by weight of hexamethyldisiloxane and approximately 5% by weight of acetonitrile. Its density $D._4^{20} = 0.764$. The lower and heavier phase (III) consists of approximately 10% by weight of hexamethyldisiloxane and 90% by weight of acetonitrile. Its density $D._4^{20} = 0.782$.

2. The toluene-acetonitrile azeotrope (IV), which consists at normal pressure of 14.4% by weight of toluene and 85.6% by weight of acetonitrile, boils at 80.5° C. and has a density $D._4^{20} = 0.798$.

In accordance with the invention, then, enough acetonitrile is added to the impure hexamethyldisiloxane to permit both azeotropic mixtures to form. The azeotrope (I) of hexamethyldisiloxane and acetonitrile can then be distilled from the mixture, after preliminary distillation if necessary to separate impurities with even lower boiling points. Once it has been distilled off, this azeotrope will separate into phases II and III. Both of these phases are then easy to separate by known methods.

The pure hexamethyldisiloxane can be separated from Phase II by distilling off the acetonitrile, almost all of which passes over as an azeotrope with hexamethyldisiloxane (I). Pure hexamethyldisiloxane will remain behind in the residue and can be reused in later syntheses. It may if necessary be subjected to fractional distillation for complete purification.

Purification in accordance with the invention can also be carried out continuously by circulating the acetonitrile. One practical way of doing so is to combine the distillate derived from Phase II in the purification of the hexamethyldisiloxane with Phase I, which occurs in the distillation of the impure hexamethyldisiloxane. The lighter Phase II, which will be rich in hexamethyldisiloxane, can then be supplied continuously from this mixture, through a transfer channel or intermediate vessel for final distillation, whereas the heavier Phase III, which will be rich in acetonitrile, can be continuously added to the impure starting mixture, where it can be employed to produce the Azeotrope I to be distilled off. Although the impurities will increase in the distillation boiler throughout the process, they will be easy to draw off from time to time by known means. When the impurities are mainly toluene or a similar solvent, it will be practical in this continuous process to stop adding the acetonitrile to the mixture of hexamethyldisiloxane and impurities after the solvent has been enriched and to distill the hexamethyldisiloxane and solvent off in an intermediate fraction until pure solvent starts to distill over. This distillate will preferably be collected in the same receiver from which the impure hexamethyldisiloxane is supplied in the continuous process. When the hexamethyldisiloxane has been separated along with some of the solvent, the rest of the solvent can, along with the other impurities with higher boiling points if necessary, be directly drawn off from the distillation boiler.

The drawing illustrates one practical method of carrying out the purifying process in accordance with the invention.

In this embodiment, the mixture A (of hexamethyldisiloxane [(Me$_3$Si)$_2$O] containing 15% toluene, for example), or even an azeotrope of hexamethyldisiloxane and toluene for example, that is to be separated is introduced through a receiver 1 into a column-distillation boiler 2. Enough acetonitrile (MeCN) to initiate circulation is also pumped through the line labeled MeCN into boiler 2. Azeotrope I is then distilled, with reflux ratios ranging preferably from 1 to 8, through column 3 (which has from 20 to 45 theoretical plates) into a receiver 4, which is constructed in the form of a phase separator and in which Azeotrope I separates into a light, acetonitrile-poor Phase II (top) and a hexamethyldisiloxane-poor Phase III (bottom). Phase II flows through a receiver 5 into a column-distillation boiler 6. When boiler 6 is full of Phase II, Azeotrope I is distilled off from it through column 7 until the product in boiler 6 contains no more acetonitrile (after about 15 to 20% has been distilled off) and can be drained off as pure hexamethyldisiloxane. Column 7 can incidentally be completely continuous if necessary. The overhead I from column 7 is also fed into receiver 4. The bottom Phase III, which is constantly separating in receiver 4 flows back through line 8 into boiler 2. The contents of boiler 2 are constantly replenished from receiver 1 during distillation. As soon as boiler 2 is almost completely full of toluene, first the reflux of Phase II through line 8 and then the supply of toluene-containing hexamethyldisiloxane from receiver 1 is stopped and the residual acetonitrile and hexamethyldisiloxane returned from boiler 2 in short distillate fractions, which may contain toluene if necessary, to receiver 1 until the toluene in boiler 2 is free of them and can be drawn off pure. Columns 3 and 7 and receivers 1 and 4 are connected to the external atmosphere through a common respiratory line 9.

The process in accordance with the invention is appropriate not only for purifying hexamethyldisiloxane in solutions containing toluene like those that occur in the processing of the residues form the manufacture of semisynthetic penicillins. It can also be employed with hexamethyldisiloxane that contains other impurities from which it can not be separated by direct distillation. The process can for example be employed to separate hexamethyldisiloxane from impurities that have approximately the same boiling point as that substance or that decompose at that temperature.

One particular advantage of the azeotropic purification method in accordance with the invention is its selectivity. Technical hexamethyldisiloxane often contains sulfurous or nitrogeneous trace impurities that will remain quantitatively in the toluene following purification in accordance with the invention, whereas the azeotrope being distilled will entrain no impurities at all, permitting the recovery of an absolutely pure hexamethyldisiloxane that will satisfy even the strict demands for purity exacted by the pharmaceutical and cosmetic industries.

EXAMPLE 1

A mixture of 650 g of acetonitrile, 1300 g of hexamethyldisiloxane, and 1000 g of toluene was carefully fractionated in a laboratory distillation column with a 4-liter boiler, a 25-mm diameter, a 2200-mm filling level (filler: 4-mm porcelain saddle), and an automatic top. The reflux ratio was 8.

1st fraction: 1712 g of an azeotrope (I) of hexamethyldisiloxane and acetonitrile
  Yield: 94.8%
  B.p.: 71.4° C., two liquid phases,
  63.5% upper phase (II): appr. 95% hexamethyldisiloxane + appr. 5% acetonitrile.
  D.$_4^{20}$ 0.764; n$_D^{25}$ 1.3750.
  36.5% lower phase (III): appr. 90% acetonitrile.
  D.$_4^{20}$ 0.782; n$_D^{25}$ 1.3462.

2nd fraction: 119 g of intermediate cut
  B.p.: 71.4°–99.1° C.
  Consisting of appr. 72% hexamethyldisiloxane, appr. 37% acetonitrile, and appr. 1% toluene. 3rd fraction: 88 g of an azeotrope of toluene and hexamethyldisiloxane
  B.p.: 99.1° C.
  Consisting of 98.6% hexamethyldisiloxane and 1.4% toluene.
  D.$_4^{20}$ 0.765.

4th fraction: 69 g of intermediate cut B.p.: 99.1°–110.5° C.
  Consisting of appr. 47% hexamethyldisiloxane and appr. 53% toluene.
  Residue: appr. 950 g of toluene with no hexamethyldisiloxane or acetonitrile.

EXAMPLE 2

A mixture of 1000 g of acetonitrile, 1000 g of hexamethyldisiloxane, and 1000 g of toluene was distilled as in Example 1.

1st fraction: 1522 g of an azeotrope (I) of hexamethyldisiloxane and acetonitrile
  Yield: 95.9%
  B.p.: 71.4° C.
  Consisting of Phases II and III.

2nd fraction: 192 g of intermediate cut
  B.p.: 71.4°–80.5° C.
  Consisting of appr. 20% hexamethyldisiloxane, appr. 70% acetonitrile, and appr. 10% toluene.

3rd fraction: 281 g of an azeotrope (IV) of toluene and acetonitrile
  B.p.: 80.5° C.
  Consisting of 85.6% acetonitrile and 14.4% toluene.
  D.$_4^{20}$ 0.798; n$_D^{25}$ 1.3692.

4th fraction: 114 g of intermediate cut
  B.p.: 80.5°–110.5° C.
  Consisting of appr. 48% acetonitrile and appr. 52% toluene.
  Residue: appr. 900 g toluene with no hexamethyldisiloxane or acetonitrile.

EXAMPLE 3

2000 g of Phase II (the upper phase of the first fraction obtained in Examples 1 and 2) were fractionated with a reflux ratio of 2 in a laboratory distillation column with 12 theoretical plates and a 4-liter boiler.

1st fraction: 267 g of an azeotrope (I) of hexamethyldisiloxane and acetonitrile
B.p.: 71.4° C.
2nd fraction: 21 g of intermediate cut
B.p.: 71.4°–100° C.
Consisting of appr. 12% acetonitrile and appr. 88% hexamethyldisiloxane.

Residue: appr. 1700 g of hexamethyldisiloxane with no toluene or acetonitrile.

EXAMPLE 4

2500 g of hexamethyldisiloxane (by-product of cephalosporin manufacture with a content of 1.64% N,N-dimethylaniline and 8 ppm of sulfur in sulfurous impurities) were carefully fractionated with 300 g of toluene and acetonitrile in the distillation apparatus described in Example 1. The reflux ratio was 2 and the boiling point 71.4° C. The distillate was collected in a receiver in which it separated into a lighter upper phase (II) and a heavier lower phase (III). To maintain a constant and sufficient supply of acetonitrile in the distillation boiler, the lower phase (III), which was 90% acetonitrile, of the distillate collected in the receiver, which was the azeotrope (I) of hexamethyldisiloxane and acetonitrile, was continuously returned during distillation through a line that could be blocked off and that had been specially installed for the purpose from the bottom outlet of the receiver to the boiler.

Finally, 2480 g of an upper phase (II) consisting of 95% hexamethyldisiloxane was obtained as a single distillate fraction. The residue (appr. 600 g), consisting of appr. 28% acetonitrile, appr. 49% toluene, another appr. 16% of hexamethyldisiloxane, and appr. 7% N,N-dimethylaniline was contaminated with 33.2 ppm of sulfur.

Distilling the 2480 g of the upper phase (II) of the distillate resulted in approximately 385 g of first runnings consisting mainly of Azeotrope I and approximately 2000 g of extremely pure hexamethyldisiloxane uncontaminated with sulfur or nitrogen.

EXAMPLE 5

A laboratory apparatus like that in the flow chart was employed. It consisted, first, of a distillation boiler 2 in the form of a 4-liter multinecked flask (heated with a heating hood) equipped with an internal thermometer, an inlet tube (in the capacity of acetonitrile return 8), and a 1-liter dropping funnel (in the capacity of receiver 1 for raw-material feed and tailing fraction), second, of a column 3 (with a diameter of 25 mm, a filling level of 2200 mm, and a 4-mm porcelain saddle as a filler) with a liquid-separator top, third, of a distillate receiver 4 in the form of a phase separator (a 1000-ml dropping funnel with two distillate-inlet tubes from columns 3 and 7 immersed to a filling level of approximately 500 ml, a bottom outlet into acetonitrile-return 8, and a separately respirated overflow tube leading into receiver 5), fourth, of an overflow receiver 5 (a 1-liter dropping funnel) with a line discharging into the middle inlet of column 7, which was continuously driven in this case, the overhead from which was also fed into receiver 4, and which had a boiler that consisted of a heatable 4-liter multineck flask provided with an overflow in the form of a communicating tube for the pure hexamethyldisiloxane that would occur in it.

Before the test began, approximately 500 g of acetonitrile were placed in distillation boiler 2. During the distillation, approximately 19 kg of hexamethyldisiloxane (containing appr. 15% toluene and 68 ppm of organic sulfur impurities) obtained as the by-product of penicillin manufacture were gradually fed in through receiver 1 with a reflux ratio of 2 until boiler 2 was full of toluene. The azeotrope I of hexamethyldisiloxane and acetonitrile was distilled from boiler 2 through column 3 at an overhead temperature of 71.4° C. into receiver 4, where it separated into the two liquid phases II (upper phase: 95% $(Me_3Si)_2O + 5\%$ MeCN) and III (lower phase: 10% $(Me_3Si)_2O + 90\%$ MeCN). The lower phase, III, was continuously returned to boiler 2, eliminating the need to feed fresh acetonitrile into the system. The upper phase, II, flowed over continously into receiver 5, from which column 7 was continuously charged. Azeotrope I was also distilled from column 7 at a reflux ratio of 2 and an overhead temperature of 71.4° C. into receiver 4 (appr. 16–17% of the product flowing into the column). The highly purified hexamethyldisiloxane was continuously removed from the overflow to boiler 6.

When a total of approximately 18.8 kg of starting material had been supplied and the boiler was full, acetonitrile reflux 8 was closed, so that almost all of the acetonitrile in the system collected in the form of the lower Phase III in receiver 4. Meanwhile, another 1.2 kg of the starting mixture was fed into the boiler through receiver 1 until almost no more acetonitrile remained in column 3.

The flow was then switched from receiver 4 to receiver 1 and an intermediate cut of approximately 550 g distilled (for subsequent use) in receiver 1 while the boiling point increased from 71.4° to 110.5° C. At a boiling point of 110.5° C. and with the top of the column set for reflux, approximately 3 kg of toluene were emptied from boiler 2. Column 3 could subsequently, after boiler 2 was refilled from receiver 1 and the acetonitrile-containing lower Phase III refilled from receiver 4 and following a brief purifying distillation into receiver 1, continue operation with pure Azeotrope I as an overhead for receiver 4, as described above.

When column 3 had gone through eight cycles of this type with column 7 operating continuously, about 160 kg of the hexamethyldisiloxane by-product with a content of 68 ppm of organic sulfur impurities and about 15% toluene had been processed in the presence of only 500 g of acetonitrile in constant circulation between boiler 2, receiver 4, and column 7. Approximately 136 kg of hexamethyldisiloxane (b.p. 100° C., extremely pure, and without any toluene or sulfurous or nitrogenous impurities) and approximately 24 kg of technical-grade toluene with a content of approximately 424 ppm of organically bound sulfur and approximately 132 ppm of organically bound nitrogen were obtained.

It will be understood that the specification and examples are illustrative but not limitative of the present invention and that other embodiments within the spirit and scope of the invention will suggest themselves to those skilled in the art.

What is claimed is:

1. Process for purifying hexamethyldisiloxane which process comprises distilling hexamethyldisiloxane in an azeotropic mixture with acetonitrile, separating the specific lighter phase from the azeotrope, and separating the hexamethyldisiloxane from the acetonitrile by distillation to recover said hexamethyldisiloxane.

2. Process as claimed in claim 1, wherein said azeotropic mixture of hexamethyldisiloxane and acetonitrile is formed from the specific heavier phase of the azeotrope of hexamethyldisiloxane and acetonitrile.

3. Process as claimed in claim 1, wherein the distillate containing acetonitrile is reintroduced into the process at a suitable point.

4. Process as claimed in claim 1 carried out continuously wherein the azeotrope of hexamethyldisiloxane and acetonitrile is produced in a first distillation boiler and fractionally distilled through a first distillation column into a separator, from which the lighter phase is allowed to overflow through a receiver into a second distillation boiler, wherein the acetonitrile is stripped in the form of its azeotrope with hexamethyldisiloxane from the lighter phase by fractional distillation through a second distillation column and transferred to said separator from which the specific heavier phase is fed into a said first distillation boiler.

5. Process as claimed in claim 4, wherein after the impurities have accumulated in said first distillation boiler, the line from said separator to said boiler is closed and said first distillation column connected operatively to a reservoir, with an intermediate fraction containing hexamethyldisiloxane being distilled through said column into said reservoir, and maintaining said intermediate fraction therein until the hexamethyldisiloxane is completely distilled over, whereupon the residual impurities are drawn off from the reservoir.

* * * * *